United States Patent

Kimoto et al.

[11] Patent Number: 4,943,675
[45] Date of Patent: Jul. 24, 1990

[54] ANILINOPYRIMIDINE DERIVATIVES

[75] Inventors: Takahiro Kimoto, Fuji; Hideo Ohi, Shizuoka; Toshihisa Watanabe, Fuji; Tadashi Nakayama, Shizuoka, all of Japan

[73] Assignee: Ihara Chemical Industry Co., Ltd., Tokyo, Japan

[21] Appl. No.: 366,459

[22] Filed: Jun. 15, 1989

[30] Foreign Application Priority Data

Jun. 24, 1988 [JP] Japan .................. 63-156069

[51] Int. Cl.$^5$ .................. C07D 239/00; C07D 239/42
[52] U.S. Cl. ........................ 544/330; 544/332
[58] Field of Search ............... 544/330, 332

[56] References Cited

FOREIGN PATENT DOCUMENTS 0224339 6/1987 European Pat. Off. .
0270111 6/1988 European Pat. Off. .
0310550 9/1988 European Pat. Off. .

Primary Examiner—Robert Gerstl
Assistant Examiner—Philip I. Datlow
Attorney, Agent, or Firm—Oblon, Spivak, McClelland, Maier & Neustadt

[57] ABSTRACT

Anilinopyrimidine derivatives of the formula:

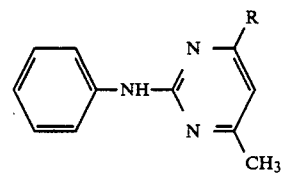

wherein R is —CH$_2$C(O)CH$_3$ or —CH=C(Cl)CH$_3$, are useful as intermediates in the production of anilinopyrimidine fungicides.

2 Claims, No Drawings

ANILINOPYRIMIDINE DERIVATIVES

The present invention relates to intermediates for the production of pyrimidine derivatives useful as fungicides. Particularly, the present invention relates to anilinopyrimidine derivatives useful as intermediates for the production of anilinopyrimidine derivatives of the formula:

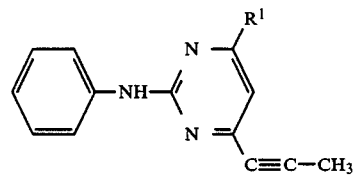

wherein R¹ is a lower alkyl group, known as fungicides as disclosed in European Patent Publication No. 224,339.

For the production of the above anilinopyrimidine derivatives of the formula II, the following process is proposed in European Patent Publication No. 224,339:

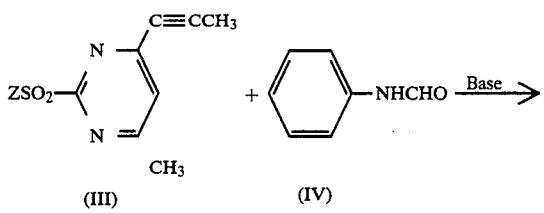

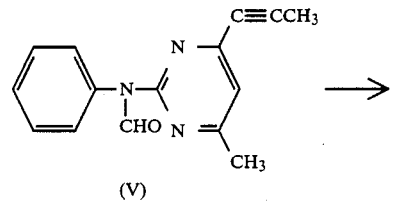

In the above formulas, Z is an alkyl group.

However, the pyrimidine compound of the formula III to be used in this process is hardly available. Therefore, it has been desired to develop another method for the production of the anilinopyrimidine of the formula II.

Under these circumstances, the present inventors have conducted extensive researches to develop a process for producing the anilinopyrimidine of the formula II efficiently on an industrial scale. As a result, they have found it possible to produce it by the following steps.

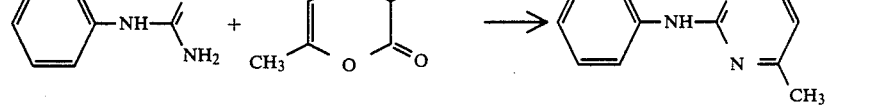

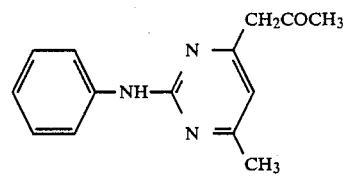
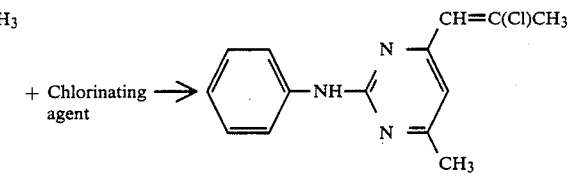

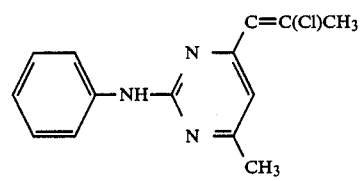
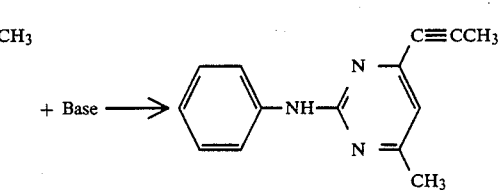

Further, it has been found that the anilinopyrimidine derivatives of the formulas VIII and IX in the above reaction scheme are novel compounds which have not been disclosed in any literatures. The present invention has been accomplished on the basis of these discoveries.

The present invention provides an anilinopyrimidine derivative of the formula:

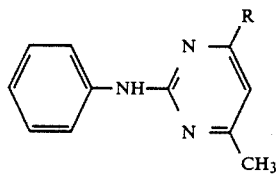

(I)

wherein R is —CH$_2$C(O)CH$_3$ or —CH=C(Cl)CH$_3$.

Now, the present invention will be described in detail with reference to the preferred embodiments.

The compounds of the present invention are anilinopyrimidine derivatives of the formula I wherein R is —CH$_2$C(O)CH$_3$ or —CH=C(Cl)CH$_3$. Among the compounds of the present invention, the compound of the formula I wherein R is —CH$_2$C(O)CH$_3$ (the compound of the formula VIII in the above reaction scheme) can be prepared by reacting the phenylguanidine of the formula VI and the dehydroacetic acid of the formula VII in a polar solvent at a temperature of at least 70° C., preferably from 100° to 150° C. It may also be produced by reacting heptane-2,4,6-trione or 2,6-dimethylpyran-4-one with the phenylguanidine of the formula VI. The phenylguanidine used in this reaction can be produced by reacting aniline and aminocyanide in a usual manner, and the resulting phenylguanidine salt is treated with a base to use it as phenylguanidine in a free form. The base used here may be an inorganic salt such as sodium hydroxide, potassium hydroxide, barium hydroxide, potassium carbonate, potassium hydrogen carbonate, sodium carbonate, sodium hydrogen carbonate or an organic base such as pyridine, piperidine or diethylamine.

Further, by reacting the obtained anilinopyrimidine with a chlorinating agent at a temperature of at least 0° C., preferably from 50° to 100° C., it is possible to obtain an anilinopyrimidine of the formula I wherein R is —CH=C(Cl)CH$_3$ (the compound of the formula IX in the foregoing reaction scheme). As the chlorinating agent useful for this reaction, phosphorus pentachloride, phosphorus oxychloride or phosphorus trichloride may, for example, be mentioned. This reaction can be conducted in the absence of a solvent. However, If necessary, it can be conducted in an inert solvent. As such an inert solvent, benzene, toluene, chlorobenzene, dichlorobenzene, chloroform, ethylenedichloride or xylene may, for example, be mentioned.

Further, by reacting this anilinopyrimidine of the formula IX with a base at a temperature of from —20° to 200° C., preferably from —10° to 150° C., it is possible to obtain the desired anilinopyrimidine of the formula II. As the base useful for this reaction, sodium hydroxide, potassium hydroxide, sodium hydride, sodium amide, a metal alkoxide such as sodium ethoxide, sodium tert-butoxide or potassium tert-butoxide, or KF/Al$_2$O$_3$ i.e. potassium fluoride supported on alumina, may, for example, be mentioned. It is preferred to use a metal tert-alkoxide such as sodium tert-butoxide or potassium tert-butoxide, among them. Such a base may be used in the solid state (powder) or in the form of an aqueous solution. This reaction is conducted in an inert solvent. As such an inert solvent, a solvent of aromatic hydrocarbon type such as toluene, xylene, benzene or chlorobenzene, an aprotic polar solvent such as dimethylformamide, dimethylacetamide, sulfolane or acetonitrile, an ether solvent such as ethyl ether, tetrahydrofuran or diethylene glycol dimethyl ether (diglyme), or an alcohol solvent such as isopropyl alcohol, tert-butyl alcohol or tert-amyl alcohol, may, for example, be mentioned. The solvent is suitably selected depending upon the type of the base used. For example, when an alkali metal hydroxide such as sodium hydroxide or potassium hydroxide is used as the base, it is preferred to employ a tertiary alcohol such as tert-butyl alcohol or tert-amyl alcohol, or it is preferred to use a mixture of such a tertiary alcohol with a hydrocarbon solvent such as n-hexane, petroleum ether, cyclohexane, toluene or xylene. The reaction may be conducted in the presence of a phase transfer catalyst such as tetrabutylammonium chloride, tetrabutylammonium bromide, tetrabutylphosphonium chloride or tetrabutylphosphonium bromide, for the purpose of smoothly carrying out the reaction.

The compounds of the formula I of the present invention are useful as intermediates for the production of known anilinopyrimidines useful as fungicides. By using the compounds of the present invention as the starting materials, it has been made possible to produce the desired anilinopyrimidines in good yield on an industrial scale, as compared with the conventional processes.

Now, the present invention will be described in detail with reference to Examples. However, it should be understood that the present invention is by no means restricted to such specific Examples.

EXAMPLE 1

Preparation of 2-anilino-4-methyl-6-acetonyl-pyrimidine (VIII)

Into a 500 ml reaction flask equipped with a stirrer, a thermometer and a condenser, 200 ml of dimethylformamide, 13.8 g (0.1 mol) of potassium carbonate, 39.6 g (0.2 mol) of phenylguanidine nitrate and 33.6 g (0.2 mol) of dehydroacetic acid were charged, and the reaction was conducted at 140° C. for 3 hours. After completion of the reaction, the reaction solution was cooled and put into ice water. Then, the reaction solution was extracted with toluene and washed with water. Then, 21 g (0.2 mol) of concentrated hydrochloric acid was dropwise added thereto. Precipitated crystals were collected by filtration, washed with toluene, then neutralized with an aqueous sodium carbonate solution and again extracted with toluene. This toluene layer was washed with water and concentrated to obtain 24.1 g of 2-anilino-4-methyl-6-acetonyl-pyrimidine having a melting point of from 77° to 80° C. The yield was 50%.

From the following results of analyses, the product was confirmed to be the desired compound.

IR(KBr): 740 cm$^{-1}$, 1240 cm$^{-1}$, 1440 cm$^{-1}$, 1530 cm$^{-1}$ $^1$H-NMR(CDCl$_3$, δ): 1.9(s), 2.2(s), 2.3(s), 3.6(s), 5.1(s), 6.0(s), 6.4(s), 6.8–7.7(m), 13.8(br)

Partially in the form of enol in CDCl$_3$.

Mass(m/e): 241(M$^+$)

EXAMPLE 2

Preparation of 2-anilino-4-methyl-6-(2-chloropropen-1-yl)pyrimidine (IX)

Into a 500 ml reaction flask equipped with a stirrer, a thermometer, a condenser and a dropping funnel, 48.3 g (0.2 mol) of 2-anilino-4-methyl-6-acetonyl-pyrimidine and 200 ml of toluene were charged and dissolved. To this solution, 61.4 g (0.4 mol) of phosphorus oxychloride was dropwise added from the dropping funnel. The mixture was reacted at a temperature of from 88° to 90° C. for further 6 hours. The reaction mixture was cooled and put into a water/toluene solution and subjected to liquid separation. The toluene layer was washed with an aqueous sodium carbonate solution and then with water. The toluene layer was concentrated to obtain 49 g of 2-anilino-4-methyl-6-(2-chloropropen-1-yl)pyrimidine having a melting point of from 63° to 66° C. The yield was 94.4%.

From the following results of analyses, the product was confirmed to be the desired compound.

IR(KBr): 740 cm$^{-1}$, 1250 cm$^{-1}$, 1550 cm$^{-1}$
$^1$H-NMR(CDCl$_3$, δ): E:Z=1:1 mixture, 2.3(s), 2.25(s), 2.35(s), 2.55(s), 6.2–6.5(m), 6.8–7.8(m)
Mass(m/e): 259(M+)

EXAMPLE 3-1

Preparation of
2-anilino-4-methyl-6-(1-propynyl)-pyrimidine (II)

Into a 500 ml reaction flask equipped with a stirrer, a thermometer and a condenser, 51.9 g (0.2 mol) of 2-anilino-4-methyl-6-(2-chloropropen-1-yl)pyrimidine and 400 ml of xylene were charged and dissolved. To this solution, 160 g (0.4 mol) of a 10% sodium hydroxide aqueous solution and 6.4 g (0.02 mol) of tetrabutylammonium bromide were added, and the mixture was reacted under reflux for 5 hours. The reaction mixture was cooled and subjected to liquid separation. The xylene layer was washed with water. The xylene layer was concentrated and subjected to column chromatography to obtain 22.8 g of 2-anilino-4-methyl-6-(1-propynyl)pyrimidine having a melting point of from 125° to 126° C. The yield was 51.1%.

EXAMPLE 3-2

Preparation of
2-anilino-4-methyl-6-(1-propynyl)pyrimidine (II)

Into a 100 ml reaction flask equipped with a stirrer, a thermometer and a condenser, 5.2 g (0.02 mol) of 2-anilino-4-methyl-6-(2-chloropropen-1-yl)pyrimidine, 1.3 g (0.024 mol) of finely pulverized KOH and 50 ml of toluene were charged, and the mixture was reacted for 10 hours under reflux. The reaction mixture was cooled, water was added, and the mixture was subjected to liquid separation. The toluene layer was washed with water. The toluene layer was concentrated and subjected to column chromatography to obtain 1.67 g of 2-anilino-4-methyl-6-(1-propynyl)pyrimidine having a melting point of from 125° to 126° C. The yield was 37.4%.

EXAMPLE 3-3

Preparation of
2-anilino-4-methyl-6-(1-propynyl)pyrimidine (II)

Into a 50 ml reaction flask equipped with a stirrer, a thermometer and a condenser, 5.2 g (0.02 mol) of 2-anilino-4-methyl-6-(2-chloropropen-1-yl)pyrimidine, 2.4 g (0.06 mol) of NaOH powder and 50 ml of acetonitrile were charged, and the mixture was reacted at room temperature for 5 hours. After the reaction, toluene and water were added to the reaction mixture, followed by liquid separation. The toluene layer was washed with water. The toluene layer was concentrated and subjected to column chromatography to obtain 1.67 g of 2-anilino-4-methyl-6-(1-propynyl)pyrimidine having a melting point of from 125° to 126° C. The yield was 36%.

EXAMPLE 3-4

Preparation of
2-anilino-4-methyl-6-(1-propynyl)pyrimidine (II)

Into a 50 ml reaction flask equipped with a stirrer, a thermometer and a condenser, 1.30 g (0.005 mol) of 2-anilino-4-methyl-6-(2-chloropropen-1-yl)pyrimidine and 10 ml of anhydrous tetrahydrofuran were charged and dissolved, and then the mixture was cooled to −10° under stirring in a nitrogen gas atmosphere. Then, 1.28 g (0.0114 mol) of potassium tert-butoxide was dissolved in 10 ml of anhydrous tetrahydrofuran and dropwise added thereto at a temperature of from −8° to −12° C., and the mixture was stirred at −15° C. for one hour. Then, 5 ml of 1N hydrochloric acid was dropwise added thereto, and 50 ml of water and a small amount of sodium hydrogen carbonate were added to bring the pH of the aqueous layer to 7. Then, the mixture was extracted with 70 ml of toluene, and the extract was dried over anhydrous sodium sulfate. The toluene layer was concentrated and subjected to silica gel column chromatography (n-hexane/ethyl acetate=10/1) to obtain 1.04 g of 2-anilino-4-methyl-6-(1-propynyl)-pyrimidine having a melting point of from 125° to 126° C. The yield was 93.2%.

EXAMPLE 3-5

Preparation of
2-anilino-4-methyl-6-(1-propynyl)pyrimidine (II)

Preparation of KF/alumina

In a 100 ml round bottom flask, 14.5 g (0.25 mol) of KF was dissolved in 25 ml of water, and 25 g of alumina was then added and dispersed in the solution. The mixture was dried at 50° C. under 30 mmHg for one hour and at 75° C. under 5 mmHg for two hours, whereupon the water content was measured by a Karl Fischer moisture meter and found to be about 10%.

Into a 50 ml round bottom flask, 0.52 g (0.02 mol) of 2-anilino-4-methyl-6-(2-chloropropen-1-yl)pyrimidine, 4.0 g of KF/alumina and 20 ml of anhydrous acetonitrile were charged, and the mixture was stirred at room temperature for 5 hours in the flask equipped with a calcium chloride tube. Then, the mixture was subjected to filtration to remove the solid content, and the solvent was distilled off. The residue was dissolved in toluene and washed with water. This toluene layer was washed with water and concentrated, and then it was subjected to column chromatography to obtain 0.3 g of 2-anilino-4-methyl-6(1-propynyl)pyrimidine having a melting point of from 125° to 126° C. The yield was 67%.

EXAMPLE 3-6

Preparation of 2-anilino-4-methyl-6-(1-propynyl) pyrimidine (II)

Into a 100 ml reaction flask equipped with a stirrer and a thermometer, 5.2 g (0.02 mol) of 2-anilino-4-methyl-6-(2-chloropropen-1-yl)pyrimidine and 40 ml of t-butanol were charged, and the mixture was heated to 60° C. Then, 4.49 g (0.08 mol) of potassium hydroxide powder was added thereto, and the mixture was reacted for 6 hours. After completion of the reaction, the mixture was put into water and extracted with toluene. The toluene layer was washed with water and concentrated, and then it was subjected to column chromatography to obtain 2.48 g of 2-anilino-4-methyl-6-(1-propynyl)-pyrimidine as slightly yellow crystals. The yield was 55.5%.

EXAMPLE 3-7
Preparation of 2-anilino-4-methyl-6-(2-propynyl)pyrimidine (II)

The operation was conducted in the same manner as in Example 3-6 except that 40 ml of t-butanol used as the solvent in Example 3-6 was changed to a solvent mixture comprising 80 ml of t-butanol and 20 ml of n-hexane, and the reaction temperature was changed from 60° C. to 5°–8° C., to obtain 3.99 g of 2-anilino-4-methyl-6-(1-propynyl)pyrimidine. The yield was 89.6%.

We claim:
1. The compound, 2-anilino-4-methyl-6-acetonyl-pyrimidine.
2. The compound, 2-anilino-4-methyl-6-(2-chloropropen-1-yl)pyrimidine.

* * * * *